United States Patent [19]

Cosyns et al.

[11] Patent Number: 4,571,442
[45] Date of Patent: Feb. 18, 1986

[54] PROCESS FOR SELECTIVELY HYDROGENATING ACETYLENE IN A MIXTURE OF ACETYLENE AND ETHYLENE

[75] Inventors: Jean Cosyns, Maule; Jean-Paul Boitiaux, Paris, both of France

[73] Assignee: Institut Francais du Petrole, Rueil-Malmaison, France

[21] Appl. No.: 652,035

[22] Filed: Sep. 19, 1984

[30] Foreign Application Priority Data

Sep. 19, 1983 [FR] France ............... 83 14969

[51] Int. Cl.⁴ .................................. C07C 5/08
[52] U.S. Cl. ........................ 585/261; 585/259; 208/255
[58] Field of Search ............ 585/261, 259; 208/255

[56] References Cited

U.S. PATENT DOCUMENTS

| | | | |
|---|---|---|---|
| 3,051,647 | 8/1962 | White | 208/255 |
| 3,131,233 | 4/1964 | Belt | 585/261 |
| 3,200,165 | 8/1965 | Eisenlohr et al. | 585/259 |
| 3,472,763 | 10/1969 | Cosyns et al. | 208/255 |
| 3,654,129 | 4/1972 | Bloch | 208/255 |
| 3,670,041 | 6/1972 | Juhl et al. | 585/258 |
| 3,865,716 | 2/1975 | Sosnowski | 208/255 |
| 4,131,537 | 12/1978 | Winter et al. | 208/255 |
| 4,347,392 | 8/1982 | Cosyns et al. | 585/259 |
| 4,409,410 | 10/1983 | Cosyns | 585/259 |

*Primary Examiner*—William R. Dixon, Jr.
*Assistant Examiner*—Cynthia A. Prezlock
*Attorney, Agent, or Firm*—Millen & White

[57] ABSTRACT

Acetylene is selectively hydrogenated by passing a mixture of acetylene and ethylene with a hydrocarbon liquid phase through a bed of a palladium-on-alumina catalyst. The liquid phase comprises an aromatic hydrocarbon and a primary or secondary amine.

18 Claims, 1 Drawing Figure

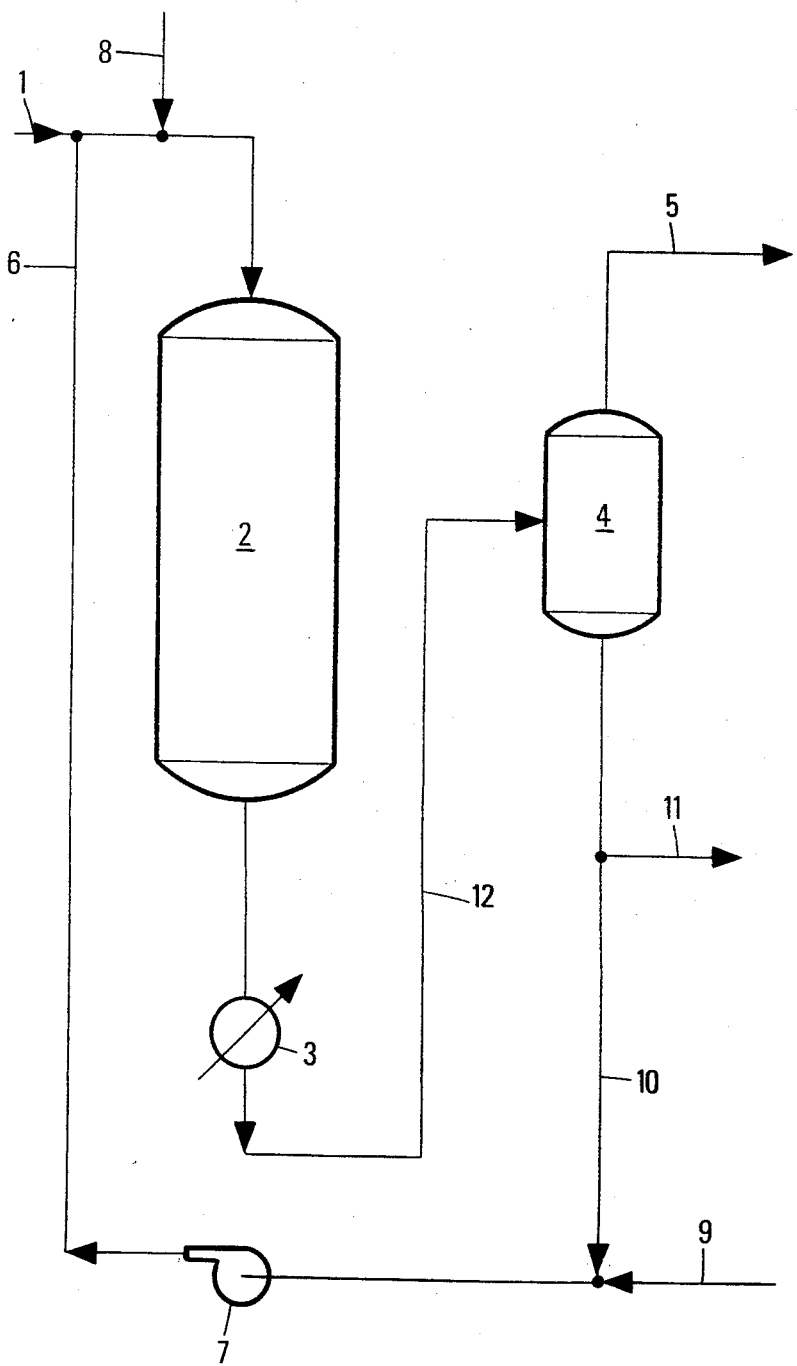

PROCESS FOR SELECTIVELY HYDROGENATING ACETYLENE IN A MIXTURE OF ACETYLENE AND ETHYLENE

The olefinic and diolefinic hydrocarbons produced by thermal conversion processes such as for example, steam cracking, are always obtained with more unsaturated hydrocarbons, particularly acetylenic hydrocarbons.

By selectively hydrogenating the latter monoolefinic and diolefinic hydrocarbons are produced, which can meet conventional specifications.

BACKGROUND OF THE INVENTION

These hydrogenations are performed with selective catalysts, for example palladium on alumina.

Nevertheless the present catalytic processes are not entirely satisfactory; the yields, as a matter of fact, are often lower than 100% and the stability of the catalyst is generally insufficient.

These difficulties are illustrated hereinafter in relation with the hydrogenation of a $C_2$ cut.

The ethylenic $C_2$ cut, as obtained from a steamcracking unit, has generally the following composition:
  acetylene—1 to 2% by volume
  ethylene—70 to 90% by volume
  ethane—10 to 30% by volume The acetylene content of the ethylenic cut must be reduced to 2 ppm by volume, or less, by selective hydrogenation of acetylene over a palladium catalyst. This result has been obtained, up to now, by isothermal or adiabatic processes, mostly operating in gas phase under about 20 to 30 bars at a temperature usually ranging from 60° to 150° C.

These processes suffer from many disadvantages:
  The exothermicity of the reaction requires the use of several reactors in series, since the gas phase is not favorable to heat removal. Moreover, the catalyst is used in large amount: a gas space velocity of 2 000 vol/vol/hour (corresponding to about 3 tons of catalyst for treating 10 t/h of $C_2$ cut) is usual.
  The catalyst is not perfectly selective. The potential ethylene yield being 101 to 102%, the yields are hardly above 99.5%. Two factors are responsible for these low yields: an insufficient selectivity resulting in an excessive production of ethane and a parasitic polymerization of acetylene to more or less heavy products often called "green oils".
  These polymers settle on the catalyst and substantially reduce the length of the runs.

Processes involving the use of a solvent have already been described for the hydrogenation of acetylene. A process of this type is disclosed in U.S. Pat. No. 4,128,595 wherein the proposed solvent is an inert hydrocarbon. The use of a solvent offers several advantages as compared with the gas phase hydrogenation process, particularly the following advantages:
  better control of the reaction exothermicity,
  improvement of the hydrogenation selectivity and hence of the ethylene yield,
  improvement of the catalyst activity and stability.

OBJECT OF THE INVENTION

The object of the present invention is to provide a new catalytic process for the selective hydrogenation of a mixture of acetylene and ethylene, operated under mild conditions and whereby activity, selectivity and life time of the catalyst are surprisingly improved.

The invention is applicable particularly to ethylene cuts produced by steam-cracking.

SUMMARY OF THE INVENTION

The process of the invention comprises selectively hydrogenating acetylene in the presence of a palladium-onalumina catalyst, in an organic liquid phase (generally comprising one or more hydrocarbons), said liquid phase comprising at least one aromatic hydrocarbon, in a proportion of 15 to 100% by weight, and an amine compound in solution therein. The process results in a substantial improvement of the ethylene yield and the catalyst stability.

A similar hydrogenation is disclosed in Belgian Pat. No. 564 339, with the use of the above-mentioned catalyst of palladium on a carrier such as calcium or barium carbonate, barium sulfate, active carbon or silica gel, in the presence of an amine of heterocyclic type consisting of quinoline or pyridine or in the presence of a solvent selected from water, alcohols and non-aromatic hydrocarbons.

In contrast thereto, according to the present invention, it is essential that the liquid phase comprise at least one aromatic hydrocarbon, for example benzene, toluene, ethylbenzene or a naphtha or kerosene cut comprising at least one aromatic hydrocarbon, so that the aromatic hydrocarbon(s) content by weight of the liquid phase used as solvent is at least 15%.

The hydrocarbon(s) of the liquid phase is (are) preferably so selected that it (they) can be easily separated from the hydrogenation products; preferably said hydrocarbon(s) have a higher boiling point than the treated cut.

In addition, it is essential to use an amine or a polyamine in a proportion from 0.01 to 10%, preferably from 0.1 to 1% by weight of the hydrocarbon(s) of the liquid phase. The amine (or each amine group of the polyamine) is either primary or secondary, and the hydrocarbon chain thereof is, for example, aliphatic or cyclic; examples thereof are butylamine, ethylamine, diethylamine, trimethylamine, piperidine, morpholine, piperazine, ethylenediamine and diethylenetriamine. The amine may comprise substituents or other groups, for example, alcohol or ether groups (e.g. morpholine, ethanolamine or diethanolamine. The amines of heterocyclic structure such as quinoline or pyridine, form no part of the invention.

The hydrogenation catalyst consists of supported palladium. Palladium is generally deposited in a proportion from 0.01 to 1% by weight on an alumina carrier. A second metal such as silver or gold may be associated to palladium, in a proportion which may range, for example, from 0.01 to 1% of the catalyst weight. Preferably, the ratio by weight (Au/Pd) or (Ag/Pd) is lower than 1. Gold gives particularly interesting results, the ratio by weight (Au/Pd) being preferably from 0.05 to 0.5.

A non-limitative embodiment of the process of the invention is illustrated by the accompanying drawing.

BRIEF DESCRIPTION OF THE DRAWING

The accompanying drawing shows a flow-sheet of the hydrogenation process according to the invention, performed in a reactor wherein the catalyst is arranged as fixed bed. It illustrates the application of the invention to hydrogenation of a $C_2$ cut.

With reference to the drawing, the cut subjected to hydrogenation (1) is introduced with hydrogen (8) and liquid diluent (6) into reactor (2). The resultant liquid-gas mixture is cooled in exchanger (3), and then introduced through line (12) into flash drum (4) wherein the purified gas cut (5) is separated from the liquid diluent (10) which is recycled through pump (7). Line (11) is provided for purging a part of the solvent and line (9) for introducing additional solvent.

The operating conditions of the $C_2$ cut hydrogenation are as follows:

space velocity, expressed as flow rate by volume of gaseous $C_2$ cut per volume of catalyst and per hour under standard conditions (gas VVH): 500 to 20,000, preferably 1,000 to 10,000.
Total pressure: 10 to 50 bars.
Temperature: 20° to 150° C.

The hydrogen flow rate is usefully adjusted in relation with the acetylenic hydrocarbons content. It is expressed in moles of hydrogen per mole of acetylenic hydrocarbons introduced into the reactor. This ratio will generally range from 1 to 10 and preferably from 1 to 2.

The solvent flow rate (hydrocarbon+amine) is usefully adjusted in relation with the catalyst volume. It is expressed as volumes of liquid charge per volume of catalyst and per hour (liq. VVH). This value is generally from 1 to 10.

The amine content of the liquid hydrocarbon phase is from 0.01 to 10% by weight and preferably from 0.1 to 2% by weight.

EXAMPLES

The following examples are given for illustrating the invention and its performances in a non-limitative manner.

EXAMPLE 1 (comparative)

This example illustrates the use of a known technique. The gas cut contains 99% by weight of ethylene and 1% by weight of acetylene. No liquid diluent is used. The catalyst contains 0.2% by weight of palladium deposited on an alumina carrier of 70 $m^2/g$ specific surface and 0.6 cc/g pore volume. The catalyst is used as fixed bed in a tubular reactor.

The $C_2$ cut is passed through the reactor in the following conditions:
gas VVH: 2,500
pressure: 25 bars
temperature: 25° C.
$H_2$/acetylene: 2 moles/mole The composition of the $C_2$ cut after 5 hours of run is as follows:
acetylene: 100 ppm
ethylene: 98.15% by weight
ethane: 1.84% by weight The ethylene yield, expressed as the ratio of the ethylene output to the ethylene input is only 99.15%.

The test is continued for 50 hours under the same conditions. The following composition of the $C_2$ effluent is obtained:
acetylene: 0.20% by weight
ethylene: 99.50% by weight
ethane: 0.30% by weight It is apparent that the catalyst activity has decreased since the conversion to ethylene is only 80% at the end of the test (acetylene content: 1% by weight at the input, 0.2% by weight at the output).

EXAMPLE 2

In this example, the same cut as in example 1 was treated under the same operating conditions, except that the ratio $H_2$/acetylene was adjusted to obtain the desired acetylene conversion. However the value of this ratio remained between 1.5 and 2 moles/mole.

A solvent was added to the $C_2$ cut and passed therewith through the catalyst bed at a rate corresponding to a liquid VVH of 5.

The solvent was recovered in a separating drum and recycled as indicated in the joint drawing.

Various solvents were used. Table 1 summarizes the results. The ethylene yields obtained with the use of different solvents are reported. This yield is given for respectively 2 ppm and 100 ppm of residual acetylene.

TABLE 1

| SOLVENTS | ETHYLENE YIELD % | |
|---|---|---|
| | 100 ppm of residual acetylene | 2 ppm of residual acetylene |
| Heptane | 100.38 | 100.22 |
| Dimethylformamide | 100.48 | —* |
| Benzene | 100.61 | 100.47 |
| Benzene + 0.2% by weight of piperidine | 100.69 | 100.65 |

*an acetylene content of 2 ppm could not be obtained even with a $H_2$/acetylene ratio of 2 moles/mole.

It is apparent that benzene with addition of 0.2% by weight of piperidine provides for the best ethylene yield.

With the above charge the theoretical yield is 101%, assuming that all acetylene is selectively converted to ethylene. The process of the invention thus provides for the conversion of 65% of acetylene to ethylene, even when acetylene is substantially completely converted.

EXAMPLE 3

This example concerns the hydrogenation of the same $C_2$ cut as in example 1 but with various solvents as used in example 2. The charge and the operating conditions are the same as in example 2. The tests have been extended over 50 hours. The operation has also been conducted with the use, as amine, of 0.2% quinoline and 0.2% pyridine (amines not conforming with the invention).

Table 2 indicates the residual acetylene content at the 5th and the 50th hour.

TABLE 2

| SOLVENTS | RESIDUAL ACETYLENE (ppm) | |
|---|---|---|
| | 5 hours | 50 hours |
| Dimethylformamide | 122 | 4 950 |
| Heptane | 1.5 | 50 |
| Benzene | 1 | 10 |
| Benzene + 0.2% by weight of piperidine | 1 | 2 |
| Benzene + 0.2% by weight of quinoline | 1.5 | 4 |
| Benzene + 0.2% by weight of pyridine | 1.5 | 5 |

It is observed that the use of an aromatic hydrocarbon containing an amine according to the process of the invention provides for both a better activity and a better stability of the catalyst.

EXAMPLE 4

This example relates to the hydrogenation of the same $C_2$ cut as in example 1.

Various liquid solvents, respectively n-heptane, toluene and a naphtha cut distilling within the range of 35°–170° C. and containing 20% by weight of aromatic hydrocarbons, are added to the $C_2$ cut, at a rate corresponding to a liquid VVH of 5. Piperidine is added to each solvent in a proportion of 0.2% by weight. The operating conditions are the same as in example 2.

Table 3 summarizes the results. The ethylene yields obtained with these different solvents for residual acetylene contents of 2 and 100 ppm are reported therein. The advantage of operating in the presence of an aromatic solvent is apparent.

TABLE 3

| SOLVENTS | ETHYLENE YIELDS | |
|---|---|---|
| | 100 ppm of acetylene | 2 ppm of acetylene |
| Heptane + 0.2% piperidine | 100.62 | 100.50 |
| Toluene + 0.2% piperidine | 100.72 | 100.69 |
| Naphtha (with 20% of aromatics) + 0.2% piperidine | 100.68 | 100.63 |

EXAMPLE 5

In this example the hydrogenation of the $C_2$ cut is performed with the various solvents used in example 4. The charge and the operating conditions are the same as in example 2. The tests were extended over 50 hours. Table 4 indicates the residual acetylene content obtained at the 5th and the 50th hour.

TABLE 4

| SOLVENTS | RESIDUAL ACETYLENE (ppm) | |
|---|---|---|
| | 5 hours | 50 hours |
| Heptane + 0.2% piperidine | 1 | 4 |
| Toluene + 0.2% piperidine | 1 | 1.5 |
| Naphtha + 0.2% piperidine | 1 | 2 |

EXAMPLE 6

The same $C_2$ cut as in example 1 is hydrogenated under the same operating conditions as in example 2. The $C_2$ cut with added toluene is passed over the catalyst bed at a rate corresponding to a liquid VVH of 5. Various amine compounds, consisting respectively of butylamine, diethylamine, ethanolamine and ethylene diamine, are added to this toluene in a proportion of 0.2% by weight.

Table 5 summarizes the results obtained with acetylene residual contents of 100 and 2 ppm.

TABLE 5

| SOLVENTS | ETHYLENE YIELD % | |
|---|---|---|
| | 100 ppm of residual acetylene | 2 ppm of residual acetylene |
| Toluene + 0.2% butylamine | 100.68 | 100.65 |
| Toluene + 0.2% diethylamine | 100.64 | 100.57 |
| Toluene + 0.2% ethanolamine | 100.67 | 100.65 |
| Toluene + 0.2% ethylenediamine | 100.70 | 100.67 |

EXAMPLE 7

The hydrogenation of the $C_2$ cut is performed with the various solvents used in example 6. The charge and the operating conditions are the same as in example 2. The tests are extended over 50 hours. Table 6 indicates the content of residual acetylene obtained at the 5th and the 50th hour.

TABLE 6

| SOLVENTS | RESIDUAL ACETYLENE (ppm) | |
|---|---|---|
| | 5 hours | 50 hours |
| Toluene + 0.2% butylamine | 1 | 2 |
| Toluene + 0.2% diethylamine | 1 | 3 |
| Toluene + 0.2% ethanolamine | 1 | 2.5 |
| Toluene + 0.2% ethylenediamine | 1 | 2 |

EXAMPLE 8

A $C_2$ cut containing 98% by weight of ethylene and 2% by weight of acetylene is hydrogenated in the same conditions as in the above examples.

Toluene with an additional content of 0.1% ethylene diamine is used as solvent. Comparative hydrogenations are performed with two catalysts conforming with the invention and respectively containing 0.2% by weight palladium deposited on alumina and 0.2% by weight palladium with the further addition of 0.05% by weight gold, these metals being deposited on alumina. Table 7 summarizes the results obtained when the residual acetylene contents are respectively 100 and 2 ppm. It is thus made obvious that the presence of gold improves the results.

TABLE 7

| catalyst | ETHYLENE YIELD | |
|---|---|---|
| | 100 ppm of residual acetylene | 2 ppm of residual acetylene |
| Palladium alone | 101.2 | 100.8 |
| Palladium + Gold | 101.5 | 101.3 |

EXAMPLE 9

The $C_2$ cut of example 8 is hydrogenated in the conditions of example 8. The tests are extended over 200 hours. Table 8 indicates the acetylene residual content at the 5th and the 200th hour. Here also the favorable effect of gold is observed.

TABLE 8

| catalyst | RESIDUAL ACETYLENE | |
|---|---|---|
| | 5 hours | 200 hours |
| Palladium alone | 3 | 6 |
| Palladium + Gold | 3 | 3 |

What is claimed as the invention is:

1. A process for the selective hydrogenation of acetylene in a mixture of acetylene and ethylene, wherein said mixture is passed through a palladium-on-alumina catalyst, in the presence of a liquid phase comprising at least one hydrocarbon, said liquid phase containing 15 to 100% by weight of at least one aromatic hydrocarbon and further containing at least one amine compound dissolved in the liquid phase and selected from the group consisting of primary amines, secondary amines and polyamines, so as to increase the overall content of ethylene in the resultant mixture.

2. A process according to claim 1, wherein the concentration of the amine compound is from 0.1 to 1% by weight of hydrocarbon in the liquid phase.

3. A process according to claim 1, wherein the amine compound is selected from the group consisting of butylamine, ethylamine, diethylamine, triethylamine, piperidine, morpholine, piperazine, ethylenediamine, triethylenediamine and ethanolamine.

4. A process according to claim 1, wherein the amine compound is selected from the group consisting of piperidine, ethylenediamine, ethanolamine, diethylamine and butylamine.

5. A process according to claim 1, wherein the catalyst contains 0.01 to 1% by weight of palladium.

6. A process according to claim 1, wherein the catalyst contains 0.01 to 1% by weight of palladium and 0.01 to 1% by weight of at least one metal selected from the group consisting of silver and gold.

7. A process according to claim 6, wherein the ratio by weight of said metal to palladium is lower than 1.

8. A process according to claim 7, wherein the ratio by weight of gold to palladium is 0.05–0.5.

9. A process for the selective hydrogenation of acetylene in a mixture of acetylene and ethylene, wherein said mixture is passed through a palladium-on-alumina catalyst, in the presence of a liquid phase comprising at least one hydrocarbon, said liquid phase containing 15 to 100% by weight of at least one aromatic hydrocarbon and further containing 0.01 to 10% by weight of hydrocarbon of at least one amine compound dissolved in the liquid phase and selected from the group consisting of primary amines, secondary amines and polyamines so as to increase the overall content of ethylene in the resultant mixture.

10. A process according to claim 9, wherein the concentration of the amine compound is from 1 to 10% by weight of hydrocarbon in the liquid phase.

11. A process according to claim 9, wherein the amine compound is selected from the group consisting of butylamine, ethylamine, diethylamine, triethylamine, piperidine, morpholine, piperazine, ethylenediamine, triethylenediamine and ethanolamine.

12. A process according to claim 9, wherein the amine compound is selected from the group consisting of piperdine, ethylenediamine, ethanolamine, diethylamine and butylamine.

13. A process according to claim 9, wherein the catalyst contains 0.01 to 1% by weight of palladium.

14. A process according to claim 9, wherein the catalyst contains 0.01 to 1% by weight of palladium and 0.01 to 1% by weight of at least one metal selected from the group consisting of silver and gold.

15. A process according to claim 14, wherein the ratio by weight of said metal to palladium is lower than 1.

16. A process according to claim 14, wherein said metal is gold, and the ratio by weight of gold to palladium is 0.05 to 0.5.

17. A process according to claim 1 wherein said amine is aliphatic.

18. A process according to claim 9 wherein said amine is aliphatic.

* * * * *